United States Patent [19]
Jouquey et al.

[11] 4,191,697
[45] Mar. 4, 1980

[54] NOVEL STEROIDS

[75] Inventors: Alain Jouquey; Jean-Pierre Raynaud; Jean Salmon, all of Paris, France

[73] Assignee: Roussel Uclaf, Paris, France

[21] Appl. No.: 915,601

[22] Filed: Jun. 15, 1978

[30] Foreign Application Priority Data

Jun. 27, 1977 [FR] France .................... 77 19613

[51] Int. Cl.² .............................................. C07J 1/00
[52] U.S. Cl. ...................... 260/397.5; 260/239.55 R; 260/397.45
[58] Field of Search ...................................... 260/397.5

[56] References Cited
U.S. PATENT DOCUMENTS

| | | | |
|---|---|---|---|
| 3,526,648 | 9/1970 | Bertin et al. | 260/397.5 |
| 3,579,545 | 5/1971 | Bertin et al. | 260/397.5 |

FOREIGN PATENT DOCUMENTS 2115033 7/1972 France .................... 260/397.45

OTHER PUBLICATIONS

"Steroid Drugs," by Applezweig, pp. 442-443, 448-449.
J.A.C.S., vol. 72 (1950), p. 4540 article by Djerassi et al.
"Steroids" (1974) article by Kundu, pp. 155-163.

Primary Examiner—Elbert L. Roberts
Attorney, Agent, or Firm—Hammond & Littell

[57] ABSTRACT

Novel $\Delta^{1,3,5(10),6}$-estratetraenes of the formula

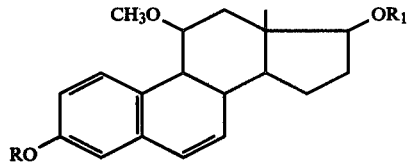

R is selected from the group consisting of hydrogen, acyl of an alkanoic acid of 1 to 5 carbon atoms, optionally substituted benzoyl, tetrahydropyranyl, trityl and trimethylsilyl and $R_1$ is selected from the group consisting of acyl of an alkanoic acid of 1 to 5 carbon atoms, optionally substituted benzoyl, tetrahydropyranyl, trityl and trimethylsilyl, novel intermediates therefore, process for the preparation of estradiols marked with a tritium atom and the novel tritiated estradiols which are useful to the study and dosage of specific receptors of estrogen.

5 Claims, No Drawings

NOVEL STEROIDS

STATE OF THE ART

British patent No. 1,151,404 and Chem. Abs., Vol. 82 (1975), p. 43644Y describe various 11β-alkoxy-Δ$^{1,3,5(10)}$-gonatrienes having estrogenic activity.

OBJECTS OF THE INVENTION

It is an object of the invention to provide the novel Δ$^{1,3,5(10),6}$-estratetraenes of formula I and novel intermediates therefore.

It is an additional object of the invention to provide a novel method of preparing tritiated estradiols and the novel estradiols produced thereby.

These and other objects and advantages of the invention will become obvious from the following detailed description.

THE INVENTION

The novel Δ$^{1,3,5(10),6}$-estratetraenes of the invention have the formula

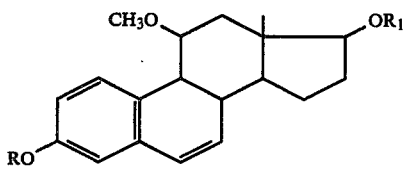

wherein R is selected from the group consisting of hydrogen, acyl of an alkanoic acid of 1 to 5 carbon atoms, optionally substituted benzoyl, tetrahydropyranyl, trityl and trimethylsilyl and $R_1$ is selected from the group consisting of acyl of an alkanoic acid of 1 to 5 carbon atoms, optionally substituted benzoyl, tetrahydropyranyl, trityl and trimethylsilyl.

Examples of suitable acyloxy groups of R and $R_1$ are those derived from alkanoic acids such as formic acid, acetic acid, propionic acid, butyric acid and valeric acid. Examples of suitable benzoyl substituents are halogens such as chlorine or bromine, alkyl of 1 to 5 carbon atoms, trifluoromethyl and alkoxy of 1 to 5 carbon atoms.

Examples of specific preferred compounds of formula I are 11β-methoxy-17β-acetoxy-Δ$^{1,3,5(10),6}$-estratetraene-3-ol and 3,17β-diacetoxy-11β-methoxy-Δ$^{1,3,5(10),6}$-estratetraene.

The novel process of the invention for the preparation of compounds of formula I comprises reacting 11β-methoxy-19-nor-testosterone with an esterification or etherification agent to form the corresponding 11β-methoxy-17β-O$R_1$-19-nor-testosterone, reacting the latter with a halogenation agent to form the corresponding 2,6-dihalo-11β-methoxy-17β-O$R_1$-Δ$^4$-estrene-3-one, reacting the latter with a deshalohydration agent to form the corresponding 11β-methoxy-17β-O$R_1$-Δ$^{1,3,5(10),6}$-estratetraene-3-ol and reacting the latter with an esterification or etherification agent to form the corresponding 3-OR-11β-methoxy-17β-O$R_1$-Δ$^{1,3,5(10),6}$-estratetraene wherein R is other than hydrogen.

In a preferred embodiment of the invention, the esterification agent to block the 17- and/or 3-positions is an alkanoic acid or a functional derivative thereof such as acetic acid anhydride or benzoyl chloride, the etherification agent to block the 17- and/or 3-positions is dihydropyran, trityl chloride or trimethylsilyl chloride, the halogenation agent is bromine in acetic acid and the deshalohydration agent is lithium chloride in dimethylformamide under an inert atmosphere.

The novel intermediates of the invention formed in the said process are 11β-methoxy-17β-acetoxy-19-nor-testosterone and 2,6-dibromo-11β-methoxy-17β-acetoxy-Δ$^4$-estrene-3-one.

The novel process of the invention for preparing steroids marked with a tritium atom from the compounds of formula I comprises reducing a compound of formula I with tritiated hydrogen in the presence of a catalyst to form [6,7-H$^3$]3-OR-11β-methoxy-17β-O$R_1$-Δ$^{1,3,5(10)}$-estratriene, subjecting the latter to the action of a strong base, a weak acid in an aqueous media or a hydrogen halide to obtain [6,7-H$^3$]11β-methoxy-Δ$^{1,3,5(10)}$-estratriene-3,17β-diol, oxidizing the latter by the Oppenhauer method with cyclohexanone in the presence of aluminum isopropylate to form [6,7-H$^3$]11β-methoxy-Δ$^{1,3,5(10)}$-estratriene-3-ol-17-one and reacting the latter with an ethynylation agent in the presence of sodium tert-amylate to obtain [6,7-H$^3$]11β-methoxy-17α-ethynyl-estradiol.

In preferred embodiments of the invention, the catalyst is hydroxide of palladium, the strong base is sodium hydroxide in methanol, the weak acid is aqueous acetic acid, the hydrogen halide is hydrochloric acid and the ethynylation agent is acetylene.

The preferred intermediates formed in the said process are [6,7-H$^3$]3,17β-diacetoxy-11β-methoxy-Δ$^{1,3,5(10)}$-estratriene, [6,7-H$^3$]11β-methoxy-Δ$^{1,3,5(10)}$-estratriene-3,17β-diol and [6,7-H$^3$]11β-methoxy-Δ$^{1,3,5(10)}$-estratriene-3-ol-17-one, with the latter two being of particular interest which lead to the formation of [6,7-H$^3$]11β-methoxy-17α-ethynyl-estradiol having a specific activity on the order of 52 Ci/mM.

The said ethynylated product permits the study and dosage of specific receptors of estrogen present in cells of the tissue or target organs of the estrogen action such as the uterus, the vagina, hypophysis, hypothalamus and tumors such as for example, breast, the prostate or adenome in animals and man. In fact, the product does not fixed itself with plasmatic proteins bonding the hormones such as testosterone and estradiol. In the female, this is a mark of the tissue receptor of estrogen with which it forms a complex of strong affinity and great stability since there is no interaction whatsoever with the tissue receptors of other classes of hormal steroids such as glucocorticoids, mineralcorticoids, androgenes or progesterones.

Finally, it permits the dosage of 11β-methoxy-17α-ethynyl-estradiol in plasma or other biological liquids for radioimmuno tests. The use of [6,7-H$^3$]11β-methoxy-17α-ethynyl-estradiol is described by Raynaud et al [Progesterone receptors in normal and neoplastic tissues, McGuire et al, Raveh Press, N.Y. (1977), p. 171–191].

The starting material, 11β-methoxy-19-nor-testosterone, is described in French Patent No. 2,115,033.

In the following examples there are described several preferred embodiments to illustrate the invention. However, it is to be understood that the invention is not intended to be limited to the specific embodiments.

EXAMPLE 1

3,17β-diacetoxy-11β-methoxy-Δ$^{1,3,5(10),6}$-estratetraene

STEP A:

11β-methoxy-17β-acetoxy-19-nor-testosterone

A solution of 15 g of 11β-methoxy-19-nor-testosterone, 75 ml of pyridine and 37.5 ml of acetic acid anhydride was stirred for 13 hours at room temperature and then, 350 ml of ice water were added thereto. The mixture was stirred for 30 minutes at 0° to 5° C. and was vacuum filtered and the filter was washed with iced water. The filtrate was evaporated to dryness under reduced pressure to obtain 16.7 g of 11β-methoxy-17β-acetoxy-19-nor-testosterone melting at +140° C. Crystallization from isopropyl ether did not change the melting point. The product had a specific rotation of $[\alpha]_D^{20} = +58.35°$ (c=1.2% in ethanol).

Analysis: $C_{21}H_{30}O_4$

|  | % C | % H | % O |
|---|---|---|---|
| Calculated: | 72.80 | 8.73 | 18.47 |
| Found: | 72.9 | 8.5 |  |

STEP B:

2,6-dibromo-11β-methoxy-17β-acetoxy-Δ$^4$-estrene-3-one

A solution of 10.78 g of bromine in 58.5 ml of acetic acid was added over 30 minutes to a solution of 11.7 g of the product of Step A in 117 ml of anhydrous ether while keeping the temperature at 20° C. and after stirring the mixture for 15 minutes, the ether was evaporated under reduced pressure at 30° C. The dry residue was taken up in 250 ml of water and the aqueous phase was extracted with methylene chloride. The organic phase was washed with a saturated aqueous sodium bicarbonate solution and then with water, was dried over anhydrous sodium sulfate to obtain a solution containing 2,6-dibromo-11β-methoxy-17β-acetoxy-Δ$^4$-estrene-3-one which was used as is for the next step.

STEP C:

11β-methoxy-17β-acetoxy-Δ$^{1,3,5(10),6}$-estratetraene-3-ol

A mixture of 10.53 g of lithium chloride and 117 ml of dimethylformamide was heated with stirring under nitrogen to +110° to 115° C. and the solution from Step B was then added thereto. The methylene chloride was distilled and the mixture was then heated for 2 hours at +110° to 115° C. under nitrogen with stirring. The mixture was cooled to +20° C. and was then poured into 500 ml of ice water. The resulting gum was extracted with methylene chloride and the organic phase was washed with an aqueous saturated sodium bicarbonate solution, then with water, was dried over sodium sulfate and evaporated to dryness under reduced pressure at +30° C. The residue was chromatographed over silica gel and was eluted with a 9-1 benzene-ethyl acetate mixture. The product was washed with benzene and was dried to obtain 4.267 g of 11β-methoxy-17β-acetoxy-Δ$^{1,3,5(10),6}$-estratetraene-3-ol melting at +189° C. The mother liquor was taken up in benzene to obtain a second yield of 860 mg of the product melting at +189° C.

STEP D:

3,17β-diacetoxy-11β-methoxy-Δ$^{1,3,5(10),6}$-estratetraene

A solution of 4.1 g of the product of Step C in 20 ml of pyridine and 10 ml of acetic acid anhydride was stirred at 20° C. for 16 hours and then 100 ml of ice and water were added thereto. The resulting gum was extracted with methylene chloride and the organic phase was washed with 1 N hydrochloric acid solution, with an aqueous saturated sodium bicarbonate solution and finally with water. The organic phase was then dried over anhydrous sodium sulfate and was then evaporated to dryness under reduced pressure to obtain 4.49 g of 3,17β-diacetoxy-11β-methoxy-Δ$^{1,3,5(10),6}$-estratetraene in the form of a colorless oil.

| U.V. Spectrum (in ethanol): | | |
|---|---|---|
| max. at 220 nm | $E_{1cm}^{1\%} = 712$ | ε =27,400 |
| Infl. towards 225 nm | $E_{1cm}^{1\%} = 656$ | |
| max. at 263 nm | $E_{1cm}^{1\%} = 223$ | ε = 8,600 |
| Inflex. towards 269–270 nm | $E_{1cm}^{1\%} = 145$ | |
| Inflex. towards 289 nm | $E_{1cm}^{1\%} = 43$ | |
| Max. at 300 nm | $E_{1cm}^{1\%} = 25$ | ε = 960 |
| U.V. Spectrum (in 0.1N ethanolic sodium hydroxide): | | |
| Max. at 241 nm | $E_{1cm}^{1\%} = 776$ | ε = 29,800 |
| Inflex. towards 267 nm | $E_{1cm}^{1\%} = 124$ | |
| Max. at 328 nm | $E_{1cm}^{1\%} = 57$ | ε = 2,200 |

EXAMPLE 2

[6,7-H$^3$]11β-methoxy-17α-ethynyl-estradiol

STEP A:

[6,7-H$^3$]3,17β-diacetoxy-11β-methoxy-Δ$^{1,3,5(10)}$-estratriene

A mixture of 45.2 mg of the product of Example 1, 10 mg of palladized carbon and 0.6 ml of redistilled ethyl acetate was cooled with liquid nitrogen and then 3.87 ml of tritium with an activity total of 10 Ci measured at 0° C. and normal pressure were added thereto. Then, the temperature of the reaction mixture was allowed to rise to room temperature and the mixture was stirred for 3 hours. Excess tritium was recovered and the mixture was filtered. The filtrate was evaporated to dryness under reduced pressure and free tritium was eliminated to obtain 46 mg of [6,7-H$^3$]3,17β-diacetoxy-11β-methoxy-Δ$^{1,3,5(10)}$-estratriene with a specific activity of 54.03 Ci/mM.

STEP B:

[6,7-H$^3$]11β-methoxy-Δ$^{1,3,5(10)}$-estratriene-3,17β-diol

A mixture of 41 mg of the product of Step A, 4 ml of redistilled methanol, 0.5 ml of water and 0.5 ml of 36° Bé sodium hydroxide solution was stirred under nitrogen and then was refluxed with stirring under nitrogen for 2 hours. The mixture was cooled to 20° C. and 0.5 ml of acetic acid and 1.5 ml of water were added thereto. The mixture was iced for one hour for crystallization and was then vacuum filtered. The product was washed with iced water and was dried under reduced pressure in the presence of phosphoric acid anhydride to obtain 30.6 mg of [6,7-H$^3$]11β-methoxy-Δ$^{1,3,5(10)}$-estratriene-3,17β-diol melting at +245° C. and having a specific activity of 52 Ci/mM.

STEP C:

[6,7-H³]11β-methoxy-Δ¹,³,⁵⁽¹⁰⁾-estratriene-3-ol-17-one

A mixture of 20.9 mg of the product of Step B and 5 ml of toluene and 2 ml of cyclohexanone was heated to 50° C. and argon was passed therethrough to distill 1 ml of toluene. Then, 1 ml of a solution of aluminum isopropylate in 50 ml of toluene were added 4 times over 30 minutes while distilling and measuring to maintain the volume constant. The mixture was refluxed for 15 minutes under argon and was then distilled while adding a solution of 1 g of sodium potassium tartrate in 10 ml of water. The solvents were then entrained with water vapor and the mixture was cooled in an ice bath to effect crystallization. The mixture was stirred at 0° C. for 30 minutes and was vacuum filtered. The product was washed with water and dried under reduced pressure in the presence of phosphoric acid anhydride at room temperature to obtain 18.8 mg of raw [6,7-H³]11β-methoxy-Δ¹,³,⁵⁽¹⁰⁾-estratriene-3-ol-17-one which was used as is for the next step.

STEP D: [6,7-H³]11β-methoxy-17α-ethynyl-estradiol

Acetylene was bubbled for 2 hours through 10 ml of a solution of 2.8 g of sodium tert-amylate per 100 ml and then a solution of the product of Step C in 2.5 ml of tetrahydrofuran was added thereto. The bubbling of acetylene was continued for 5 hours at room temperature with stirring. The bubbling of acetylene was then replaced with argon bubbling and immediately after acidification of the mixture, with 2 ml of 50% aqueous acetic acid it was cooled in an ice bath. The mixture was extracted with ether and the ether extracts were washed with water until just neutral, dried over sodium sulfate and were evaporated to dryness under reduced pressure to obtain 25 mg of product. The said product was dissolved in 1 ml of pure tetrahydrofuran which was subjected to plate migration with a 7-3 benzene-ethyl acetate mixture as the migration solvent. The product was isolated by elution with a 1-1 methylene chloride-acetone and the solution was evaporated to dryness under reduced pressure to obtain 11.1 mg of 26% solvated product equal to 8.17 mg of non-solvated [6,7-H³]11β-methoxy-17α-ethynyl-estradiol with a specific activity of 52 Ci/mM.

Various modifications of the products and processes of the invention may be made without departing from the spirit or scope thereof and it should be understood that the invention is intended to be limited only as defined in the appended claims.

We claim:

1. A compound of the formula

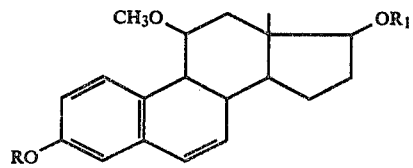

wherein R is selected from the group consisting of hydrogen, acyl of an alkanoic acid of 1 to 5 carbon atoms, benzoyl, benzoyl substituted with at least one member of the group consisting of halogen, —CF₃ and alkyl and alkoxy of 1 to 5 carbon atoms, tetrahydropyranyl, trityl and trimethylsilyl and R₁ is selected from the group consisting of acyl of an alkanoic acid of 1 to 5 carbon atoms, benzoyl, benzoyl substituted with at least one member of the group consisting of halogen, —CF₃ and alkyl and alkoxy of 1 to 5 carbon atoms, tetrahydropyranyl, trityl and trimethylsilyl.

2. A compound of claim 1 which is 11β-methoxy-17β-acetoxy-Δ¹,³,⁵⁽¹⁰⁾,⁶-estratetraene-3-ol.

3. A compound of claim 1 which is 3,17β-diacetoxy-11β-methoxy-Δ¹,³,⁵⁽¹⁰⁾,⁶-estratetraene.

4. A process for the preparation of a compound of claim 1 comprising reacting 11β-methoxy-19-nor-testosterone with an esterification or etherification agent to form the corresponding 11β-methoxy-17β-OR₁-19-nor-testosterone, reacting the latter with a halogenation agent to form the corresponding 2,6-dihalo-11β-methoxy-17β-OR₁-Δ⁴-estrene-3-one, reacting the latter with a deshalohydration agent to form the corresponding 11β-methoxy-17β-OR₁-Δ¹,³,⁵⁽¹⁰⁾,⁶-estratatraene-3-ol, reacting the latter with an esterification or etherification agent to form the corresponding 3-OR-11β-methoxy-17β-OR₁-Δ¹,³,⁵⁽¹⁰⁾,⁶-estratetraene wherein R is other than hydrogen.

5. A process for the preparation of [6,7-H³]11β-methoxy-17α-ethynyl-estradiol comprising reducing a compound of claim 1 with tritiated hydrogen in the presence of a catalyst to form [6,7-H³]3-OR-11β-methoxy-17β-OR₁-Δ¹,³,⁵⁽¹⁰⁾-estratriene, subjecting the latter to the action of a strong base, a weak acid in an aqueous media or a hydrogen halide to obtain [6,7-H³]11β-methoxy-Δ¹,³,⁵⁽¹⁰⁾-estratriene-3,17β-diol, oxidizing the latter by the Oppenhauer method with cyclohexanone in the presence of aluminum isopropylate to form [6,7-H³]11β-methoxy-Δ¹,³,⁵⁽¹⁰⁾-estratriene-3-ol-17-one and reacting the latter with an ethynylation agent in the presence of sodium tert-amylate to obtain [6,7-H³]11β-methoxy-17β-ethynyl-estradiol.

* * * * *